(12) United States Patent
Mars

(10) Patent No.: US 10,054,525 B2
(45) Date of Patent: Aug. 21, 2018

(54) INSTRUMENT FOR MEASURING THE INTRINSIC STRENGTH OF POLYMERIC MATERIALS VIA CUTTING

(71) Applicant: Endurica, LLC, Findlay, OH (US)

(72) Inventor: William V. Mars, Findlay, OH (US)

(73) Assignee: Endurica, LLC, Findlay, OH (US)

( * ) Notice: Subject to any disclaimer, the term of this patent is extended or adjusted under 35 U.S.C. 154(b) by 40 days.

(21) Appl. No.: 15/193,256

(22) Filed: Jun. 27, 2016

(65) Prior Publication Data

US 2017/0003207 A1 Jan. 5, 2017

Related U.S. Application Data

(60) Provisional application No. 62/186,593, filed on Jun. 30, 2015.

(51) Int. Cl.
*G01N 3/08* (2006.01)
*G01N 3/04* (2006.01)

(52) U.S. Cl.
CPC ............ *G01N 3/08* (2013.01); *G01N 3/04* (2013.01); *G01N 2203/0026* (2013.01); *G01N 2203/0066* (2013.01); *G01N 2203/0091* (2013.01); *G01N 2203/0092* (2013.01)

(58) Field of Classification Search
CPC ............ G01N 3/08; G01N 3/04; G01N 19/02; G01N 2203/0026; G01N 2203/0091; G01N 2203/0092; E21B 49/006
USPC .......................................... 73/783, 808, 159
See application file for complete search history.

(56) References Cited

U.S. PATENT DOCUMENTS

| | | | |
|---|---|---|---|
| 8,047,069 B2 * | 11/2011 | Coulter | G01N 3/58 73/159 |
| 9,746,401 B2 * | 8/2017 | Kanade | G01N 3/02 |
| 2007/0113671 A1 * | 5/2007 | Samples | G01N 3/32 73/808 |

OTHER PUBLICATIONS

Anil K. Bhowmick (1988): Threshold Fracture of Elastomers, Journal of Macromolecular Science, Part C: Polymer Reviews, 28:3-4, 339-370.
Lake, G. J., and O. H. Yeoh. "Measurement of rubber cutting resistance in the absence of friction." International Journal of Fracture 14.5 (1978): 509-526.
Lake, G. J., Thomas A. G., "The strength of highly elastic materials." Proceedings of the Royal Society of London. Series A. Mathematical and Physical Sciences 300.1460 (1967): 108-119.

* cited by examiner

*Primary Examiner* — Harshad R Patel
*Assistant Examiner* — Octavia Hollington
(74) *Attorney, Agent, or Firm* — Jacob M. Ward; Ward Law Office LLC

(57) ABSTRACT

A testing instrument and method for measuring the intrinsic strength of polymeric materials via cutting includes a pair of mechanical clamps connected at a base to low-friction hinges. The clamps are configured to secure the elongate edges of a polymer specimen, and to periodically load the specimen to a predetermined strain. The load on the specimen while strained is measured with an opening force load sensor. While in the strained condition, the specimen is cut with a highly sharpened blade, and the cutting force also measured by a cutting force load sensor. A cutting energy curve may be plotted from these measurements, from which a cutting energy can further be derived.

19 Claims, 7 Drawing Sheets

UNDEFORMED

FATIGUE CRACK GROWTH - DEFORMED

CRACK TIP DISSIPATION

CUTTING - DEFORMED

INSTRUMENT FOR MEASURING THE INTRINSIC STRENGTH OF POLYMERIC MATERIALS VIA CUTTING

CROSS REFERENCE TO RELATED APPLICATIONS

This application claims the benefit of U.S. Provisional Application No. 62/186,593, filed on Jun. 30, 2015. The entire disclosure of the above application is hereby incorporated herein by reference.

FIELD

The present technology relates to determining an intrinsic strength value of an elastomeric material using an apparatus that strains and cuts the elastomeric material while measuring the forces related to these actions.

BACKGROUND

This section provides background information related to the present disclosure which is not necessarily prior art.

Effective use of a given elastomer can depend on one or more properties of the elastomer and the capability to measure or quantify such properties. One property of interest is the elastomer's intrinsic strength, also referred to as the fatigue endurance limit. The intrinsic strength marks a limit below which cyclic loads may be endured by the elastomer indefinitely without incurring damage.

Determination of intrinsic strength can be important in maximizing durability and avoiding failure of the elastomer for a given application. Although intrinsic strength has been studied for decades by researchers interested in fatigue performance, measuring it has previously required either exceptionally long testing periods (months via a direct method of observation), or the use of inconvenient and potentially unsafe solvents (via an indirect method that involves swelling the elastomer and possibly changing the properties of interest).

There is a continuing need for an instrument and method for measuring the intrinsic strength of polymeric materials via cutting. Desirably, the instrument and method is efficient and does not require the use of solvents or swelling of the polymeric materials being tested.

SUMMARY

In concordance with the instant disclosure, an instrument and method for measuring the intrinsic strength of polymeric materials via cutting, and which is efficient and does not require the use of solvents or swelling of the polymeric materials being tested, is surprisingly discovered.

The present technology includes systems, processes, and articles of manufacture that relate to determining the intrinsic strength of a material, including polymeric and elastomeric materials. Ways are provided to obtain a cutting energy versus an energy release rate curve for a material and determine the intrinsic strength of the material. Articles and apparatus are provided that allow one or more measurements to be made with a single specimen of the material, where apparatus can employ a single axis of linear cutting motion under a fixed loading condition. Embodiments of the apparatus include a fixture for a specimen of material that is substantially similar to a planar tension apparatus, but where clamps holding the material rotate to produce a strain gradient such that the energy release rate of a crack decreases as the crack is lengthened through the material. A mechanism that continuously supplies a fresh blade edge such as a microtome blade for cutting can also be included in embodiments of the present technology.

In one embodiment, an apparatus for ascertaining an intrinsic strength of a polymeric material includes a pair of clamps, a first drive, a blade, and a second drive. The pair of clamps are hingedly attached to a base, and configured to secure opposing edges of a test specimen formed from the polymeric material. The first drive is connected to the clamps and configured to selectively open the clamps in an opening motion. The test specimen is strained during the opening motion of the clamps. The blade is spaced apart from the base and configured to be moved between the clamps. The second drive is connected to the blade and configured to selectively advance the blade toward the base in a cutting motion, while the test specimen is being strained.

In another embodiment, a method for ascertaining the intrinsic strength using the apparatus includes a step of measuring a thickness (t), a length (L), and a gauge height (h) of the test specimen in an undeformed state. The test specimen is then installed in the clamps. Predetermined straining and cutting operations are performed on the test specimen using the apparatus. The predetermined straining and cutting operations include cycles of unloading and reloading the test specimen. The apparatus then determines, as a function of time, an opening angle (theta) of the clamps, a crack length (c) of the test specimen, an opening force (F) that is placed on the test specimen during the opening motion of the clamps, and a cutting force (f) applied by the blade to the test specimen during the cutting motion of the blade. From these values, energy-versus-crack-length curves for the cycles of the unloading and the reloading of the test specimen are generated. A power-law slope (beta+1) is computed by means of a curve fitting process for each of the energy-versus-crack-length curves. For instants of time for which the crack length (c) was measured, an energy U(L−c), a representative strain energy density Wbar, an opening release rate (T), and a cutting energy (S) are also computed, and a cutting energy curve S(T) is then plotted. A point (Sc) on the cutting energy curve is then located, wherein Sc=minimum (T+S). The point (Sc) for the test specimen is compared to a value (Sci) obtained for a reference material of known intrinsic strength (T0i). The intrinsic strength (T0) for the test specimen is thereby ascertained, wherein T0=T0i Sc/Sci.

Further areas of applicability will become apparent from the description provided herein. The description and specific examples in this summary are intended for purposes of illustration only and are not intended to limit the scope of the present disclosure.

DRAWINGS

The above, as well as other advantages of the present disclosure, will become readily apparent to those skilled in the art from the following detailed description, particularly when considered in the light of the drawings described hereafter, in which:

FIG. 1 shows a graph defining intrinsic strength ($T_0$), in which the intrinsic strength is the energy release rate below which no crack growth occurs due to dynamic mechanical cycles, and in which the intrinsic strength can be derived from crack growth rate (mm/cycle, y-axis) and energy release rate (J/m$^2$, x-axis);

FIGS. 2A-2C show various schematic illustrations of an exemplary polymeric material having polymer chains and cross links, with FIGS. 2A and 2B depicting the polymer material failure process during a fatigue crack growth experiment, where the polymeric material is shown in both an undeformed state (FIG. 2A) and a deformed state (FIG. 2B), and with FIG. 2C depicting a polymer failure process during the herein described cutting experiment, where the polymeric material is shown in the deformed state while being cut by a blade;

DETAILED DESCRIPTION

Figure 1:
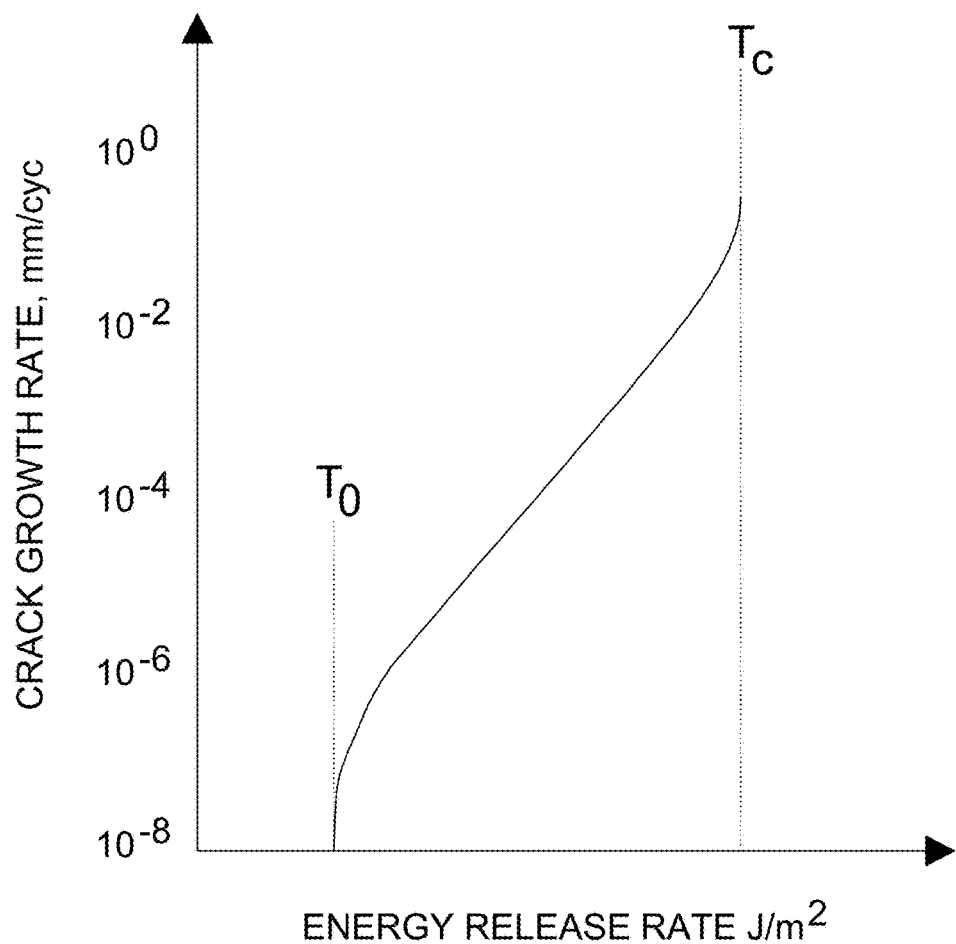

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. Except where otherwise expressly indicated, all numerical quantities in this description are to be understood as modified by the word "about" and all geometric descriptors are to be understood as modified by the word "substantially" in describing the broadest scope of the technology.

The present technology relates to determining various properties of an elastomeric material, including the intrinsic strength of the elastomer. The intrinsic strength, also known as the fatigue endurance limit, marks a limit below which cyclic loads may be endured by the elastomer indefinitely without damage incurring thereto. Determination of intrinsic strength can be important in the effective use of the elastomer and in maximizing durability and avoiding failure of the elastomer for a given application, design, or engineering purpose.

The present technology uses the principle that the fatigue endurance limit is set by the intrinsic strength of an elastomer's individual polymer network chains. Growing a crack requires that a sufficient quantity of energy be provided to rupture each polymer chain that is reached by the crack tip. The present technology can determine this minimum rupture energy, and its associated critical stress and strain levels. Under experimental conditions common to prior art strength and durability tests, the minimum energy cannot be observed directly as it is obscured by a large amount of additional energy that is consumed simultaneously in viscoelastic processes occurring near the crack tip. However, the crack tip can be probed directly for the intrinsic strength, and the effects of extraneous dissipated energy can be readily distinguished. The present technology can use a series of carefully controlled cutting steps, each made with a highly sharpened, instrumented blade, which can be executed in less than a day without the use of solvents. Results of the present technology, when compared to results obtained by way of the direct methods of observation, can demonstrate a correlation of greater than 93%.

The present technology can be used by developers and analysts who are responsible for product durability. For example, various probing and efficient diagnostic tools and options are provided for managing fatigue performance early in a development program. Developers can therefore use the present methods and measurements to select candidate materials and to obtain parameters needed to numerically simulate fatigue performance under real-world conditions and to better navigate design decisions involving complex material, geometric, and loading issues.

One property of interest with respect to an elastomer is the intrinsic strength of the elastomer. With reference to FIG. 1, the intrinsic strength or the fatigue endurance limit is defined as the minimum energy release rate $T_0$ at which a crack can possibly grow. At loads below $T_0$, the elastomer can endure an indefinite number of cycles without incurring fatigue damage. At loads between $T_0$ and the ultimate strength $T_c$, fatigue crack growth occurs at a rate depending on the energy release rate.

In certain embodiments, the present technology provides an effective way to observe a material's intrinsic strength by measurements taken during controlled cutting of a pre-strained elastomer specimen with an instrumented blade. The measurement principle is illustrated in FIGS. 2A-2C, which compares fatigue crack growth (FIGS. 2A-2B) in undeformed and deformed states with cutting (FIG. 2C) in a deformed state.

Figure 2A:
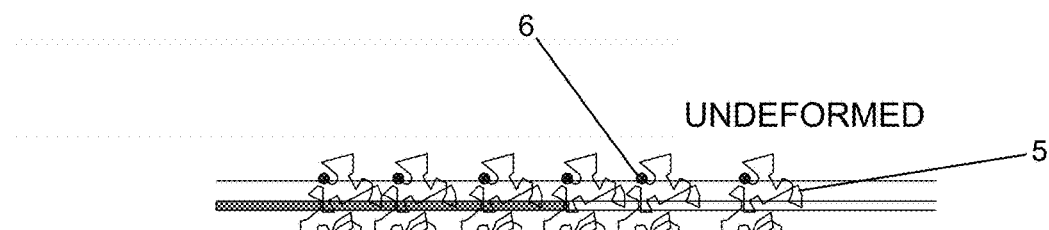
Figure 2B:
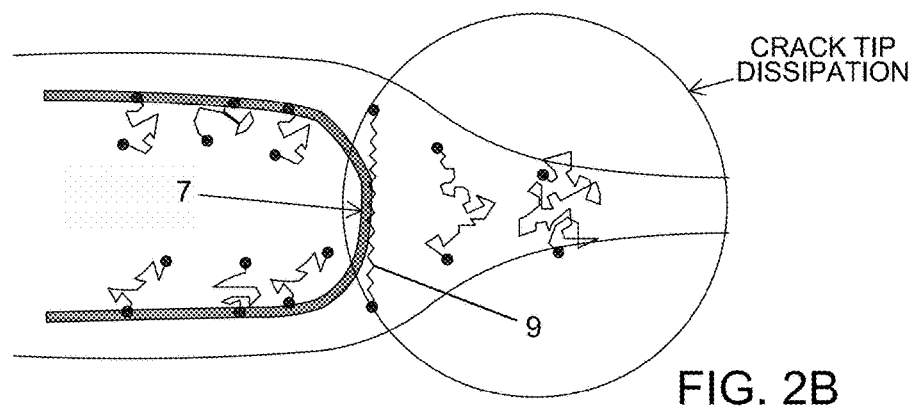
Figure 2C:
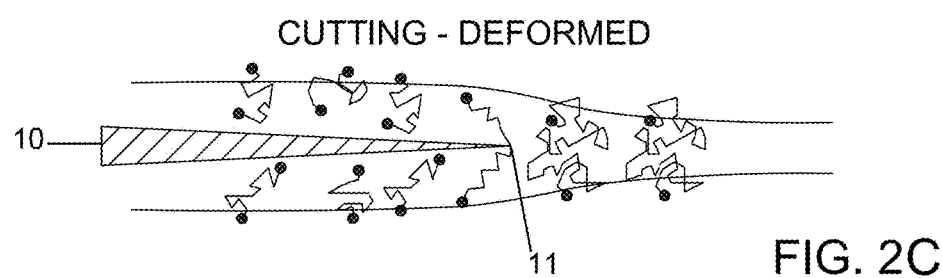

In particular, FIGS. 2A and 2B show fatigue crack growth in undeformed and deformed materials, while FIG. 2C shows cutting by a blade 10 in a deformed polymeric material, with the blade 10 represented by a triangle in FIG. 2C. In FIGS. 2A-2C, polymer chain molecules 5 spanning a thickness of the polymer material are shown in schematic form, for the purpose of illustration. Naturally, the polymeric chain molecules 5 include cross links 6. As depicted in FIG. 2B, as the polymeric material undergoes deformation, a crack tip 7 may form. At the crack tip 7, the polymer chain molecules 5 that reach a fullest extension 9 under the deformation will break 11, permitting a propagation of the crack tip 7 through the polymeric material.

Growing a crack in a polymeric material requires, at a minimum, the breaking of all polymer chain molecules 5 that cross the plane of the crack. In fatigue experiments, growing a crack also requires supplying energy to the region neighboring the crack tip 7, where strain energy may be strongly dissipated without breaking the polymer chain molecules 5. Cutting provides a direct measure of the strength of the polymer chain molecules 5 because the polymer chain molecules 5 are directly loaded by the blade 10, without the usual hysteretic dissipation incurred when crack growth is achieved via remote load application.

Figure 3:
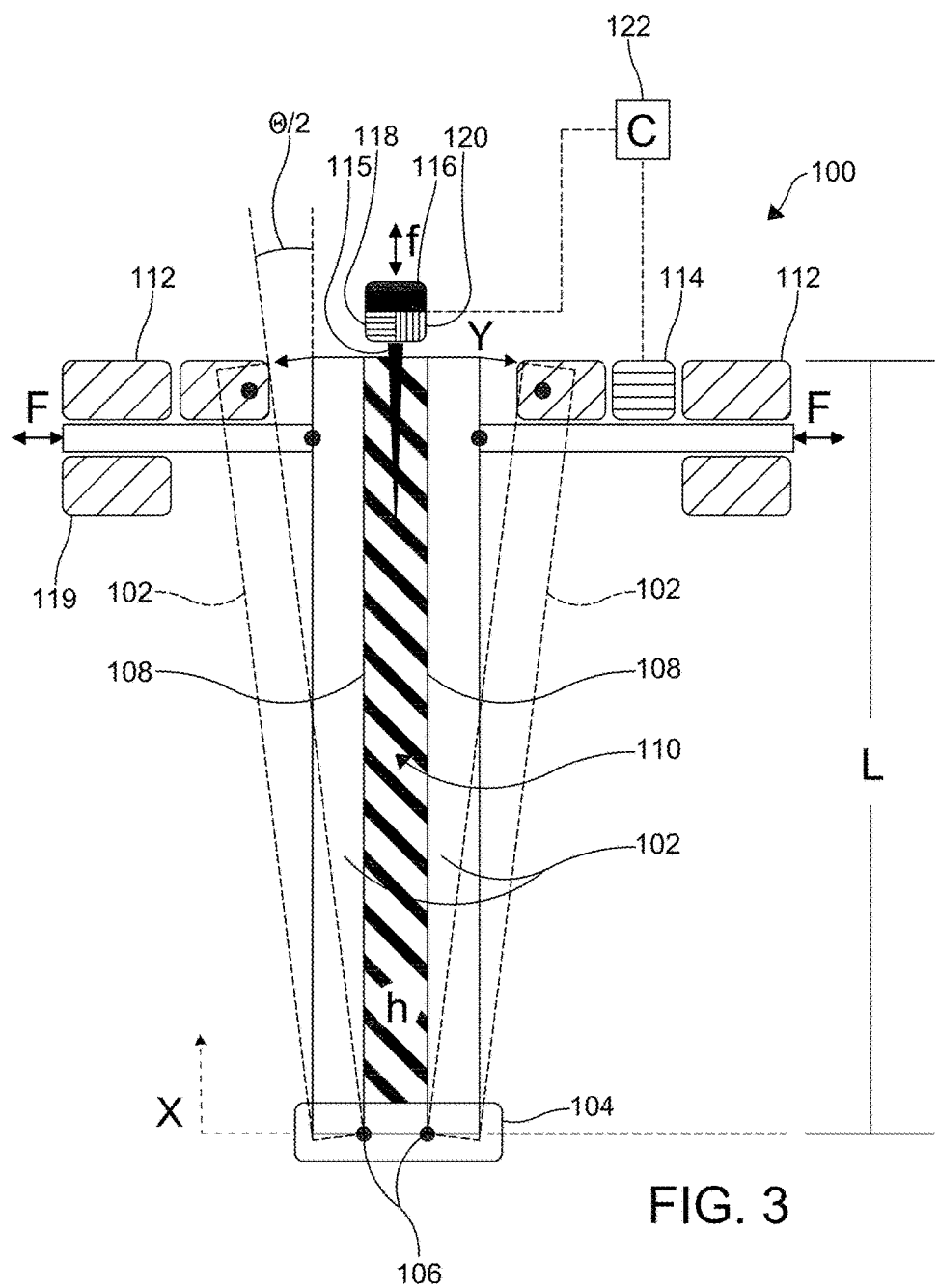
FIG. 3 shows a schematic illustration of a testing instrument for measuring the intrinsic strength of a polymeric specimen via cutting, according to one embodiment of the present disclosure.

An embodiment of an apparatus 100 for determining intrinsic strength is shown in FIG. 3. The apparatus 100 includes clamps 102 that a connected to a base 104 of the apparatus 100 with at least one low-friction hinge 106. Each of the clamps 102 may be rotatably fixed to the base at one end, and free on another end, so as to both selectively open to a substantially V-shape in operation. The clamps 102 may be quick-release specimen clamps, for example, that are configured to secure opposing edges 108 of a test specimen 110 such as a cured rubber sample and strain or stretch the test specimen 110 open while being cut for testing purposes.

To facilitate an opening motion of the clamps 102, the clamps 102 are connected to a high precision first drive 112. The first drive 112 may be a linear actuator, for example. An opening force load sensor 114 may be attached to the first drive 112 and configured to measure an opening force (F) or load that is placed on the test specimen 110 during the opening motion. Other suitable types of drives 112 for selectively causing the clamps 102 to rotate outwardly about a hinge point defined by the at least one hinge 106, and sensors 114 for measuring the opening force (F) or load, may also be used within the scope of the present disclosure.

The apparatus 100 further includes a highly sharpened blade 115 at a position spaced apart from the base 104 of the apparatus 100. The blade 115 is configured to be selectively advanced back and forth between the clamps 102, toward the base 104, and through the test specimen 110 during the cutting operation, and in particular while the test specimen 110 is strained. The blade 115 is suitable for cutting cured rubber samples. The blade 115 may be a steel, glass, or diamond microtome blade, as one non-limiting example. One of ordinary skill in the art may select suitable types of highly sharpened blades 115, as desired.

To facilitate a cutting motion of the blade 115 to cut the test specimen 110, the blade 115 is connected to a high precision second drive 116. The second drive 116 may be a linear actuator, for example. A cutting position sensor 118 and a cutting force load sensor 120 may be attached to the second drive 116. The cutting position sensor 118 is configured to measure a movement or location of the blade 115 throughout the cutting motion. The cutting force load sensor 120 is configured to measure a cutting force (f) or load that is applied by the blade 115 to the test specimen 110 during the cutting motion.

It should further be understood that the first drive 112 of the present disclosure may have a displacement sensor 119. The displacement sensor 119 is configured to measure a position or displacement (Y) of at least one of the clamps 102 during the opening motion. Where the displacement (Y) and a length (L) of the test specimen 110 (and likewise a length of the associated clamp 102) are known, it should also be appreciated that the opening angle (theta) may be readily calculated as twice the arctangent of the displacement (Y) divided by the length (L), or theta/2=A TAN(Y/L). Other types of sensors, including rotation sensors and optical sensors, as non-limiting examples, may also be used within the present disclosure to measure the opening angle (theta), as desired.

Each of the high precision linear first drive 112 for the opening motion, the high precision linear second drive 116 for the cutting motion, the opening force load sensor 114, the cutting position sensor 118, and the cutting force load sensor 120 is also in communication with a controller 122. The controller 122 may be configured to perform the testing method of the present disclosure, as described further herein. In one example, the controller 122 may be a computer with a processor and memory, which is configured to both cause the drives 112, 116 to be selectively actuated, and to receive measurement signals from the various sensors 114, 118, 120. The controller 122 permits an operation of the apparatus 100 in accordance with the present disclosure.

The controller 122 may also be configured to perform calculations as described further herein, and to generate and display on a monitor or screen (not shown) the end results of the calculations indicative of an intrinsic strength of the test specimen 110, as desired.

In operation, the clamps 102 hold the opposing edges 108 of the test specimen 110. The first drive 112 then causes one free end of each of the clamps 102 to rotate outward (e.g., to a position identified by dashed lines in FIG. 3), where a bottom of each of the clamps maintains a rotatable but otherwise fixed position about a hinge point defined by the at least one hinge 106, resulting in a straining of the test specimen 110. The stretching of the specimen 110 at the outward rotating free end imparts strain into the specimen 110, and provides an opening force indicated by the uppercase letter "F" in FIG. 3.

The second drive 116 then causes a force to push the blade 115 (i.e., a cutting force, indicated in FIG. 3 by the lowercase letter "f") into the most strained region of the specimen 100. A cut is thereby made in the specimen 110, while a strain on the specimen 100 caused by the opening force F is held constant.

In FIG. 3, a width of the polymer specimen 110 is represented by a lowercase "h." Stretch state in the specimen 110 depends on the position "X," (origin at the hinge 106) as follows:

$$\lambda_1(X) = \frac{X}{h}\sin\theta + 1$$
$$\lambda_2 = \cos\theta$$

Crack opening "g" depends on opening angle theta and length of cut:

$$g = (L-c)\sin\theta$$

$$g > t_b$$

Crack opening "g" should be greater than blade thickness $t_b$.

Figure 4:
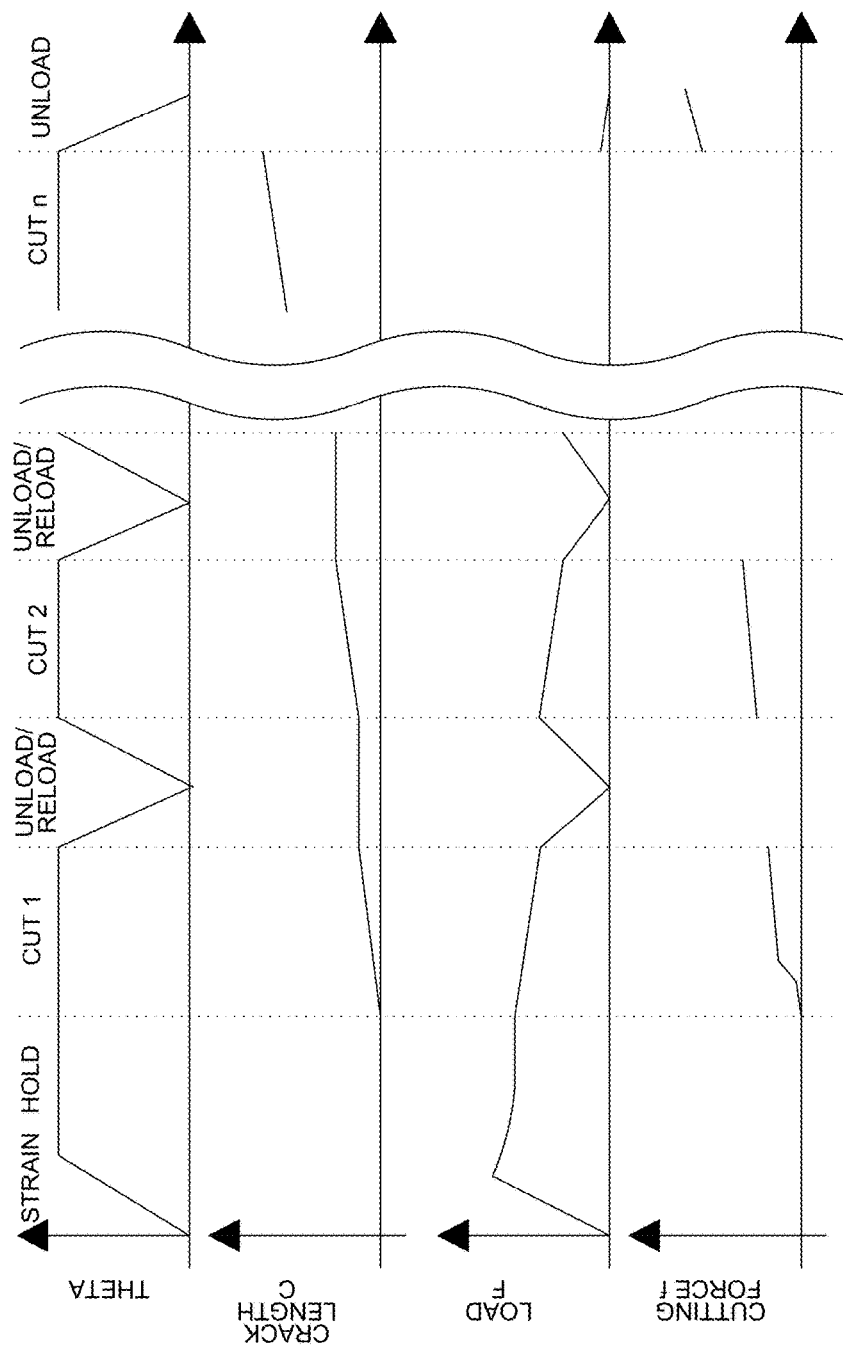
FIG. 4 shows graphs depicting an operation of the testing instrument in FIG. 3 during a testing of the polymeric specimen via cutting, according to one embodiment of the present disclosure.
Figure 5A:
FIG. 5A-5F show exemplary finite element analysis models of the polymeric specimen at various stages of cutting during operation of the testing instrument in FIG. 3.
Figure 5B:
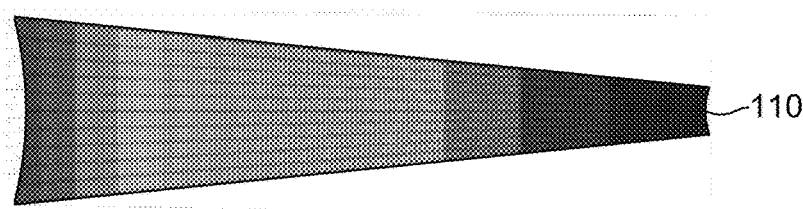
Figure 5C:
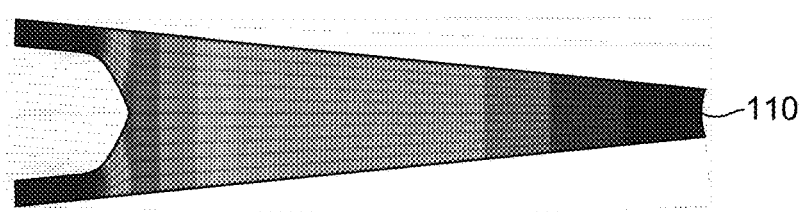
Figure 5D:
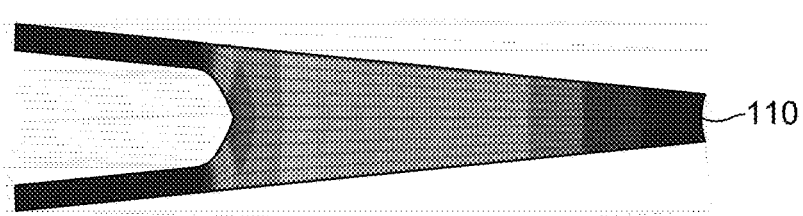
Figure 5E:
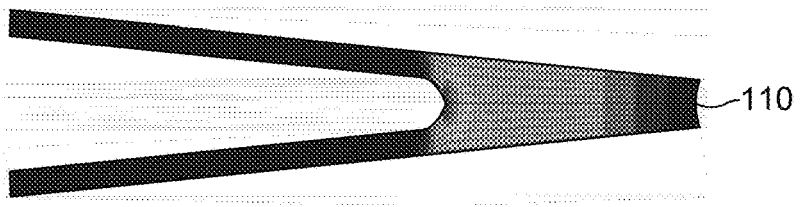
Figure 5F:
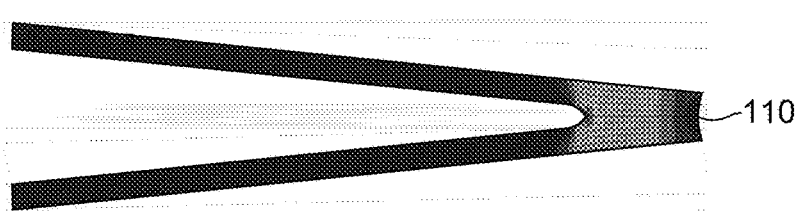

FIG. 4 depicts an example of the operation of the apparatus 100 depicted in FIG. 3. The various parameters (theta, crack length c, load F, and cutting force f) are plotted on the y-axis against time on the x-axis. As the cut grows, the blade 115 is periodically stopped, and the specimen 110 is unloaded and then reloaded to a same strain before continuing to cut with the blade 115. The periodic unloading and reloading of the specimen 110 to the same strain is performed to observe the energy at each cutting level.

An exemplary deformation of the specimen 110 during cutting and depiction of strain in the specimen 110 is illustrated in FIGS. 5A-5F. A strain gradient is shown by changing shades from the portion of the specimen 110 having the greatest deformation (at the cutting front in each panel) to the portion of the specimen 110 having the least deformation (at non-cutting end of each panel). The strain gradient can be seen to change and move as cuts progress through the specimen 110.

Results of processing the specimen 110 can then be analyzed as follows. First, the total energy U can be obtained by integrating work input FLd(theta):

$$U = \int FLd\theta$$

A representative strain energy density Wbar is also defined as follows $$\overline{W} = \frac{U(1+\beta)}{(L-c)ht} = \frac{(1+\beta)\int FLd\theta}{(L-c)ht}$$

Second, the total energy U can be obtained by integrating energy density $W(X) = KX^\beta$ with respect to X:

$$U = \int_0^{L-c} \overline{W}(x)htdx = \int_0^{L-c} Kx^\beta htdx$$

$$U = Kht\frac{(L-c)^{\beta+1}}{\beta+1}$$

Total energy can therefore be equated as:

$$\frac{\overline{W}(L-c)ht}{(1+\beta)} = U = Kht\frac{(L-c)^{\beta+1}}{\beta+1}$$

Where:

$$K = \frac{\overline{W}}{(L-c)^\beta}$$

The variations in energy dU and in crack area dA are given by $$dU=[-Kht(L-c)^\beta]dc$$

$$dA=tdc$$

The following relationship gives the energy release rate T of the cracked/cut specimen 110 as a function of representative stored energy Wbar:

$$T = -\frac{dU}{dA} = Kh(L-c)^\beta = \overline{W}h$$

Figure 6A:
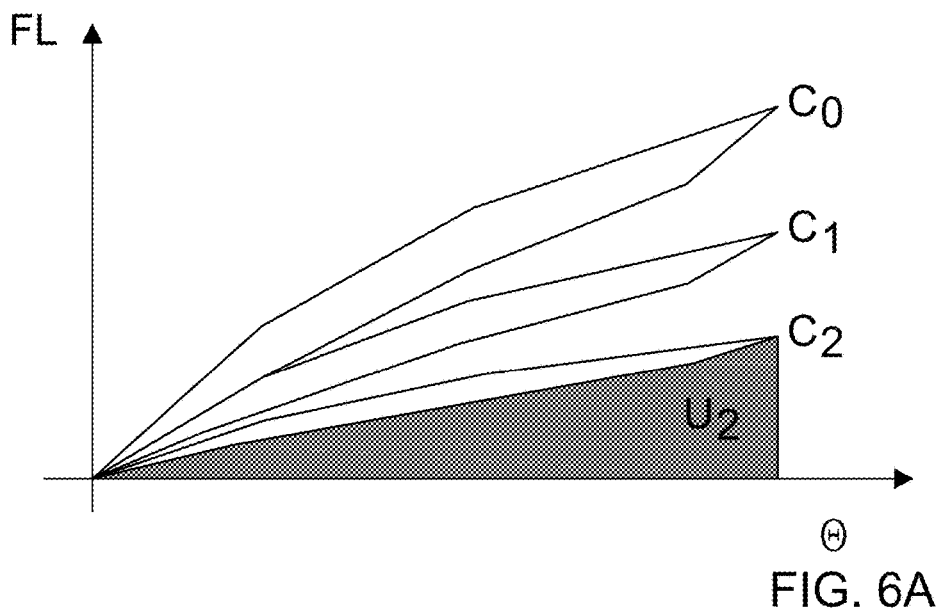
FIGS. 6A-6B show graphs describing the generation of parameters needed for energy release rate calculations.
Figure 6B:
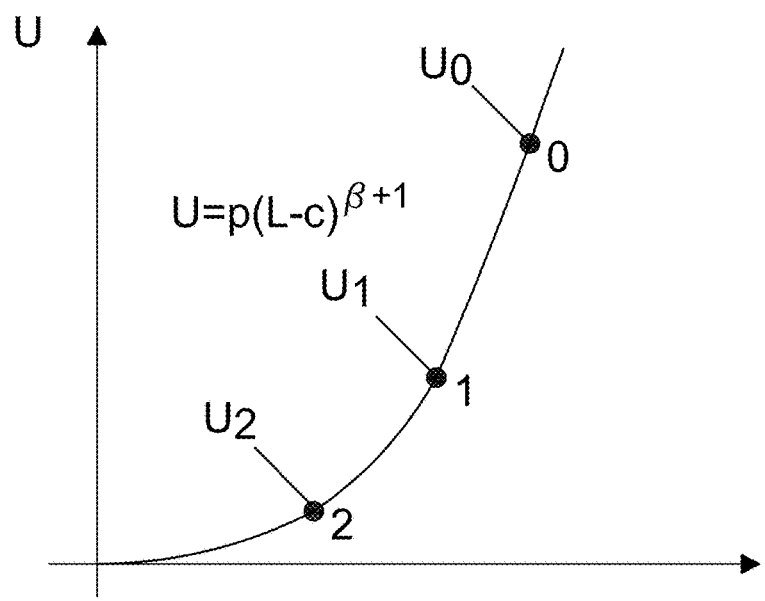

Total energy U(c) can then be measured as follows. After strain is applied, U can be measured as needed by executing an unload/reload event. The area under the unload curve at a given crack length c, as shown in FIG. 6A, gives the energy U. FIG. 6A shows how load/unload events are used to measure the F-theta curve and used for calculating the energy $U_2$ as a function of crack/cut length. FIG. 6B plots the energy U as a function of L-c, and the power-law slope of the curve fit is used to obtain the parameter beta, which is needed for the energy release rate calculations.

Figure 7:
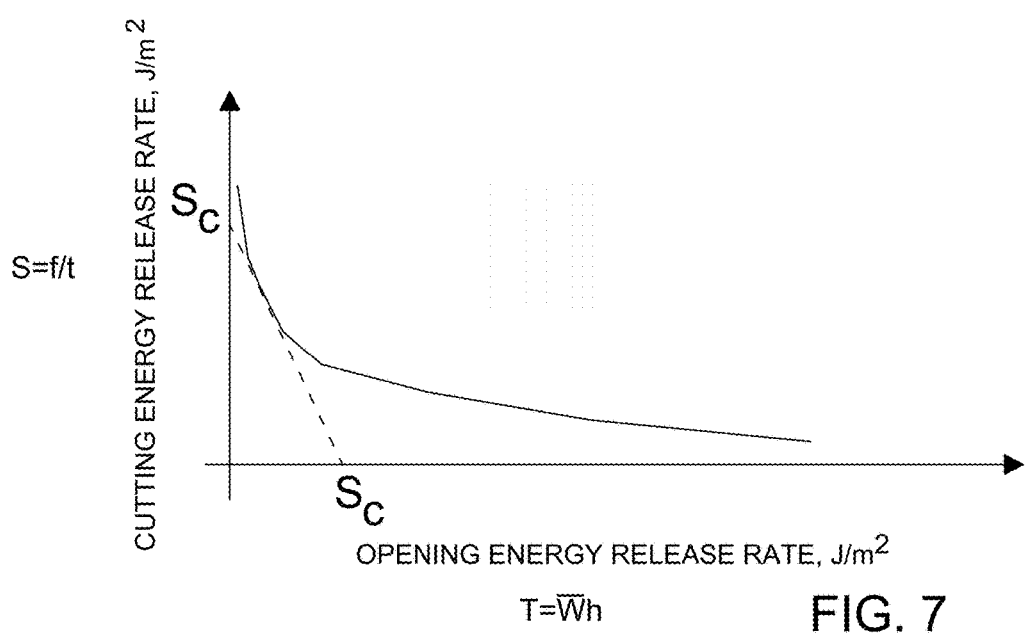
FIG. 7 shows a graph with a cutting energy curve from which a cutting energy parameter, used to calculate the intrinsic strength, may be derived.

Turning now to FIG. 7, an example of results obtained using the present technology is graphically depicted by plotting the opening energy release rate T ($J/m^2$) on the x-axis versus the cutting energy release rate S ($J/m^2$) on the y-axis. The cutting energy Sc can then be related to $T_0$. For example, a control material with a known $T_0$ value (i.e., intrinsic strength, see FIG. 1) can be analyzed using the present apparatus 100 and methods to determine the Sc for the control material. The determined Sc for a specimen 110 with an unknown $T_0$ can then be compared and related to the known $T_0$ and Sc values of the control material to determine the $T_0$ for the specimen 110. For example, $T_0$[control]/Sc[control]≈$T_0$[specimen]/Sc[specimen], so that the intrinsic strength of an unknown specimen≈Sc[specimen]×($T_0$[control]/Sc[control]). Each of these calculations can be performed using the controller 122, and the determined intrinsic strength displayed by the controller 122, for example. Thus, the present technology allows the intrinsic strength to be determined from a single test specimen 110 whereas other methods require measurements from multiple test specimens 110.

An embodiment of a method according to the present technology includes the following steps:
(a) Measure/record specimen 110 thickness t and length L in undeformed state.
(b) Install specimen in clamps 108, measure gauge height h in undeformed state.
(c) Perform the pre-programmed straining and cutting operations.
  (i) Measure theta, c, F, f as function of time.
(d) For each unload/reload in the pre-programmed operations, plot a point on the energy vs. crack length curve.
  (i) Store the corresponding value of crack length c.
  (ii) Compute the stored energy U in the specimen 110.
(e) Using the energy vs. crack length curve, compute the power-law slope beta+1 by means of a curve fitting process.
(f) For each instant of time for which crack length c is recorded:
  (i) Use the curve fit and crack length c to compute energy U(L−c)
  (ii) Compute Wbar
  (iii) Compute the opening energy release rate using T=Wbar h
  (iv) Compute the cutting energy S=f/t
(g) Plot the cutting energy curve as S(T).
(h) Find the point of the S(T) curve such that Sc=min (T+S).
(i) Compare the value of Sc for the subject material to the value Sci obtained for a reference material of known intrinsic strength T0i. Since Sc and $T_0$ are considered linearly proportional, compute the intrinsic strength $T_0$=$T_0$i Sc/Sci Examples of useful test specifications include the following:
(a) 0<theta<15 deg
(b) Unload/reload rate: 0<theta dot<15 deg/sec
(c) Cutting rate cdot: 0<cdot<10 mm/sec, typical 1 mm/min
(d) Specimen length L=150 mm
(e) Specimen gauge height 2<h<20 mm, typical 10 mm
(f) Specimen thickness 0<t<5 mm, typical 2 mm The present technology overcomes issues with other means of determining the intrinsic strength of an elastomer, where direct methods of measuring intrinsic strength can take too long, swelling methods require messy solvents and testing at multiple rates and temperatures, and other cutting methods require multiple tests at different loads. Other benefits and advantages of the present technology include a significant reduction of testing and analysis time (e.g., about 2 hours using the present technology versus 100 days or more using other methods).

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:
1. An apparatus for ascertaining an intrinsic strength of a polymeric material, comprising:
  a pair of clamps hingedly attached to a base, and configured to secure opposing edges of a test specimen formed from the polymeric material;

a first drive connected to the clamps and configured to selectively open the clamps in an opening motion, the test specimen strained during the opening motion of the clamps;

a blade spaced apart from the base and configured to be moved between the clamps;

a second drive connected to the blade and configured to selectively advance the blade through the test specimen in a cutting motion while the test specimen is being strained; and at least one sensor configured to determine, as a function of time, an opening angle (theta) of the clamps, a crack length (c) of the test specimen, an opening force (F) that is placed on the test specimen during the opening motion of the clamps, and a cutting force (f) applied by the blade to the test specimen during the cutting motion of the blade.

2. The apparatus of claim 1, wherein the apparatus includes a controller in communication with the at least one sensor.

3. The apparatus of claim 2, wherein the controller is configured to receive measurement signals from the at least one sensor, and to actuate the first drive and the second drive in response to the measurement signals and according to predetermined cutting and straining operations.

4. The apparatus of claim 3, wherein the controller has a processor and a memory, and the predetermined cutting and straining operations are embodied on the memory and executed by the processor.

5. The apparatus of claim 1, wherein the at least one sensor includes an opening force load sensor attached to the first drive and configured to measure the opening force (F) that is placed on the test specimen during the opening motion of the clamps.

6. The apparatus of claim 1, wherein the at least one sensor includes a cutting position sensor attached to the second drive and configured to measure the crack length (c) of the test specimen throughout the cutting motion of the blade.

7. The apparatus of claim 1, wherein the at least one sensor includes a cutting force load sensor attached to the second drive and configured to measure the cutting force (f) applied by the blade to the test specimen during the cutting motion of the blade.

8. The apparatus of claim 1, wherein the at least one sensor includes a displacement sensor configured to measure a position (Y) of one of the pair of clamps, from which the opening angle (theta) of the clamps may be calculated.

9. The apparatus of claim 1, wherein at least one of the first drive and the second drive is a high precision linear motor.

10. An apparatus for ascertaining an intrinsic strength of a polymeric material, comprising:

a pair of clamps hingedly attached to a base, and configured to secure opposing edges of a test specimen formed from the polymeric material;

a first drive connected to the clamps and configured to selectively open the clamps in an opening motion, the test specimen strained during the opening motion of the clamps;

a blade spaced apart from the base and configured to be moved between the clamps;

a second drive connected to the blade and configured to selectively advance the blade through the test specimen in a cutting motion while the test specimen is being strained;

a plurality of sensors, including an opening force load sensor attached to the first drive and configured to measure an opening force (F) that is placed on the test specimen during the opening motion of the clamps;

a cutting position sensor attached to the second drive and configured to measure a crack length (c) of the test specimen throughout the cutting motion of the blade;

a cutting force load sensor attached to the second drive and configured to measure a cutting force (f) applied by the blade to the test specimen during the cutting motion of the blade;

a displacement sensor configured to measure a position (Y) of one of the pair of clamps; and a controller in communication with the opening force load sensor, the cutting position sensor, and the cutting force load sensor, the controller configured to receive measurement signals including the opening force (F), the cutting force (f), the crack length (c), and the position (Y) from the plurality of sensors, and to actuate the first drive and the second drive in response to the measurement signals and according to predetermined cutting and straining operations, and wherein the controller has a processor and a memory, and the predetermined cutting and straining operations are embodied on the memory and executed by the processor.

11. A method for ascertaining an intrinsic strength of a polymeric material, the method comprising the steps of:

providing an apparatus having a pair of clamps hingedly attached to a base, and configured to secure opposing edges of a test specimen formed from the polymeric material, a first drive connected to the clamps and configured to selectively open the clamps in an opening motion, the test specimen strained during the opening motion of the clamps, a blade spaced apart from the base and configured to be moved between the clamps, and a second drive connected to the blade and configured to selectively advance the blade through the test specimen in a cutting motion while the test specimen is being strained;

measuring a thickness (t), a length (L), and a gauge height (h) of the test specimen in an undeformed state, the test specimen formed from the polymeric material;

installing the test specimen in the clamps;

performing predetermined straining and cutting operations on the test specimen using the apparatus, wherein the predetermined straining and cutting operations include cycles of unloading and reloading of the test specimen;

measuring, as a function of time, an opening angle (theta) of the clamps, a crack length (c) of the test specimen, an opening force (F) that is placed on the test specimen during the opening motion of the clamps, and a cutting force (f) applied by the blade to the test specimen during the cutting motion of the blade; and creating energy-versus-crack-length curves for the cycles of the unloading and the reloading of the test specimen;

computing a power-law slope (beta+1) by means of a curve fitting process on the energy-versus-crack-length curve;

computing, for instants of time for which the crack length (c) was measured, an energy U(L−c), a representative strain energy density Wbar, an opening release rate (T), and a cutting energy (S);

plotting a cutting energy curve S(T);

locating a point (Sc) on the cutting energy curve, wherein Sc=minimum (T+S);

comparing the point (Sc) for the test specimen to a value (Sci) obtained for a reference material of known intrinsic strength ($T_0$i); and computing the intrinsic strength ($T_0$) for the test specimen, wherein $T_0$=$T_0$i Sc/Sci, whereby the intrinsic strength ($T_0$) for the polymeric material is ascertained.

12. The method of claim 11, wherein the step of creating each energy-versus-crack-length curve includes the steps of:

storing a corresponding value of the crack length (c); and computing a stored energy (U) of the test specimen.

13. The method of claim 11, wherein the opening angle (theta) of the clamps is between 0 degrees and 15 degrees.

14. The method of claim 11, wherein an unload/reload rate during the predetermined straining and cutting operations is been 0 degrees/second and 15 degrees/second.

15. The method of claim 11, wherein a cutting rate during the cutting motion is between 0 mm/second and 10 mm/second.

16. The method of claim 11, wherein the apparatus further includes:

at least one sensor configured to determine, as a function of time, an opening angle (theta) of the clamps, a crack length (c) of the test specimen, an opening force (F) that is placed on the test specimen during the opening motion of the clamps, and a cutting force (f) applied by the blade to the test specimen during the cutting motion of the blade; and a controller in communication with the at least one sensor, the controller configured to receive measurement signals from the at least one sensor, and to actuate the first drive and the second drive in response to the measurement signals and according to the predetermined cutting and straining operations.

17. The method of claim 16, wherein the controller has a processor and a memory, and the predetermined cutting and straining operations are embodied on the memory and executed by the processor.

18. The method of claim 16, wherein the controller generates a display on a screen or monitor, the display including the intrinsic strength ($T_0$) for the test specimen.

19. The method of claim 16, wherein a user is permitted to store in the memory of the controller the thickness (t), the length (L), and the gauge height (h) of the test specimen in the undeformed state.

* * * * *